United States Patent [19]

Christen et al.

[11] 4,072,846

[45] Feb. 7, 1978

[54] CONTROL SYSTEM FOR A CHROMATOGRAPHY APPARATUS OVEN DOOR

[75] Inventors: Urs Christen, Walnut Creek; Dewayne C. Guidinger, Concord, both of Calif.

[73] Assignee: Varian Associates, Inc., Palo Alto, Calif.

[21] Appl. No.: 662,769

[22] Filed: Mar. 1, 1976

[51] Int. Cl.$^2$ ............................................. H05B 1/02
[52] U.S. Cl. .................................... 219/497; 73/23.1; 165/30; 219/531
[58] Field of Search .......................... 73/23.1; 165/30; 219/497, 499, 531; 236/249

[56] References Cited

U.S. PATENT DOCUMENTS

| 1,607,054 | 11/1926 | Chadborn | 236/49 |
| 1,952,350 | 3/1934 | Armstrong | 236/49 |
| 3,285,055 | 11/1966 | Reinecke | 165/30 |
| 3,385,101 | 5/1968 | Roof | 73/23.1 |
| 3,789,190 | 1/1974 | Orosy et al. | 219/497 |

Primary Examiner—J. V. Truhe
Assistant Examiner—Fred E. Bell
Attorney, Agent, or Firm—Stanley Z. Cole; John J. Morrissey

[57] ABSTRACT

In a chromatography system of the type including an oven for the chromatographic column, and an electric heater for controllably heating the oven, an improved system is disclosed for controllably opening and closing the oven door to enable a fully controlled heat leak, thereby to stabilize the oven temperature at a desired set point. A signal, which is indicative by first or second conditions of an oven temperature above or below the set point, is generated. A heater power control responsive to one of the signal conditions can effect heating of the oven. A bi-directional door motor and actuator means is provided for opening and closing the oven door over a prescribed operating range, and this means is enabled to operate for a predetermined period upon the signal in its first or second condition departing from preset threshold values for a predetermined period, in consequence of which the opening or closing of the oven door is effected in incremental steps.

7 Claims, 2 Drawing Figures

CONTROL SYSTEM FOR A CHROMATOGRAPHY APPARATUS OVEN DOOR

BACKGROUND OF INVENTION

This invention relates generally to chromatography systems and methodology, and more specifically relates to apparatus and techniques used in such environments for regulating oven temperatures.

Chromatographic systems commonly include an oven which surrounds the chromatographic column so as to maintain a desired operating temperature. In many instances, an operating temperature range of interest occurs at a zone slightly above ambient. Efforts to maintain the system oven temperature in such a range, have in the past taken the form on the one hand of overly complex and expensive approaches requiring the use of sophisticated and costly components, or on the other hand of relatively makeshift and by and large unacceptable techniques.

For example, coolants such as liquid nitrogen or carbon dioxide have been employed where it was necessary to produce temperatures below a minimum level established by heat produced by the oven mixing fan and by heat leaks through oven insulation from other heated zones. When desired temperatures were below this minimum level, but higher than ambient air temperature, a common but completely makeshift technique has involved manually opening the oven door to create an uncontrolled heat leak. This last approach, while somewhat effective for its purposes, produces unstable and non-repeatable results.

Within recent years, efforts have been undertaken to mechanize the door opening procedure so that the results thereof would be more stable and repeatable in nature. The techniques thus far contemplated, however, have involved simple opening and closing of the oven door in response to temperature sensor determinations, the net result of which has been to produce pulsations of cooler ambient air as the latter enters the oven chamber. In consequence, undesirable temperature gradients can occur within the oven. Detectors such as those operating on the thermal conductivity principle are highly sensitive to such gradients, and the end result is a deterioration of signal quality.

In accordance with the foregoing, it may be regarded as an object of the present invention to provide a system for controllably opening and closing the oven door in a chromatographic system in such manner that the temperature conditions within the oven may be accurately controlled and rapidly stabilized at a set temperature, without undue oscillations occuring in the system.

SUMMARY OF INVENTION

In accordance with the present invention, the foregoing object, and others as will become apparent from the ensuing specification, are achieved by means of a control system which utilizes ambient air as the available coolant, and which applies the coolant continuously and gradually over a broad temperature range according to the power requirement for the oven. A bi-directional door motor and suitable linkage are provided, which enable stepwise incremental opening and closing of the oven door over its useful range of operation. A signal generated by a sensor means positioned in the oven is provided to a comparator, along with an input from a temperature set point control. The comparator enables a heater power control whenever the sensor indicates a requirement for heating. At the same time, the output from the comparator is provided to a pair of door comparators, which can enable the bi-directional door motor in one or the other of its possible direction of movement, depending upon whether the comparator signal is sufficiently above or below preset reference points. The door comparators are, however, coupled to door opening and closing power controls, which enable the aforementioned motor through a time delay means that inhibits movement of the door unless the temperature deviation from the set point continues for a predetermined period following enablement of the heater power. This arrangement prevents the door controls from reacting to short responses that could be caused by the heater turning on, or by a previous door movement.

Each of the door opening and door closing power controls is operated for prescribed periods by means of associated timers, so that the door will open or close incrementally. These two timers have different periods, which are selected so that the door will seek a stable non-oscillating position.

BRIEF DESCRIPTION OF DRAWING

The invention is diagrammatically illustrated, by way of example, in the drawing appended hereto in which.

DESCRIPTION OF PREFERRED EMBODIMENT

Figure 1:
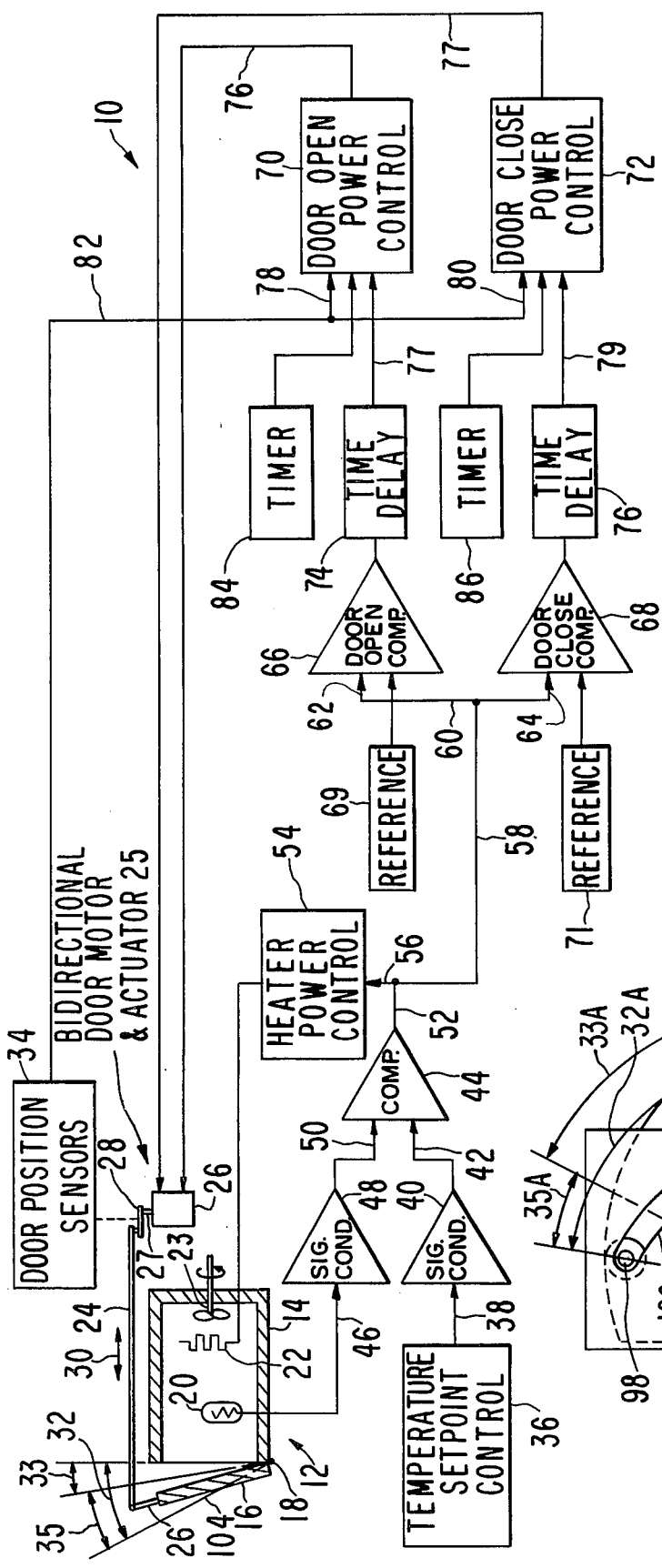
FIG. 1 is a schematic diagram showing in block form the principal electrical circuitry associated with the present system and schematically illustrating these association of these operative elements of this circuitry with the oven.

In FIG. 1 a schematic block diagram appears, setting forth the key elements forming part of a control system 10 in accordance with the invention. The control system 10 is shown associated and being utilized with a schematically depicted oven 12. Oven 12 includes an enclosure 14 which is accessable by means of an oven door 16, which may be regarded as hinged to enclosure 14 at 18. Oven 12 forms part of a chromatographic system, which is otherwise not set forth herein. It should be pointed out, as is known to those skilled in the present art, that the chromatographic column carrying the material to be analyzed passes within enclosure 14, where the column and its contents are maintained at an appropriately set temperature. A temperature sensor 20, which may be of conventional design, is mounted in the interior of enclosure 14 for sensing the temperature therein. Similarly, a heater 22 is mounted toward the rear of enclosure 14, and a mixing fan 23 is provided for assuring proper circulation of air within the enclosure to maintain uniformity of temperature.

In accordance with one aspect of the present invention the opening and closing of door 16 is enabled by a mechanical linkage 24 secured to the door at one end through a link 26. The other end of linkage 24 is actuated by a bi-directional door motor and actuator means 25, which comprises a bi-directional motor 26 having a shaft 27 that is connected to one end of a bell crank actuator 28. The other end of the bell crank actuator 28 is connected to the linkage 24 so as to cause displacement of the linkage 24 in one or the other of the directions 30 in accordance with the rotational position of the shaft 27 of motor 26. Further aspects of the actuator mechanism will be discussed hereinbelow in connection with FIG. 2.

In the normal course of operation of an apparatus according to the present invention the door 16 has a useful operating range as is schematically indicating at 32, i.e., an angular range within which the door 16 is incrementally opened and closed in order to enable the temperature control function. Door position sensors 34 are provided for establishing information with regard to the position of the door within range 32. These door position sensors 34 may take the form of limit switches, the actuating arms of which may ride upon the periphery face or on other portions of the crank disc of actuator 28. Protrusions or projections or the like displace the actuating arms of such limit switches to indicate desired information about specified door positions, including notably the end points of range 32, i.e., they establish a completely "open" position and a completely "closed" position within that operating range.

In accordance with the principles of the present invention, a temperature is initially set by an operator at the temperature set point control 36. The electrical signal proceeding in line 38 from control 36, after being suitably conditioned at conditioner 40, is provided to an input 42 of a comparator 44. The electrical signal from heat sensor 20 within oven 12 is similarly provided by a line 46 to the other input 50 of comparator 44, after first being conditioned at signal conditioner 48.

Comparator 44 provides a signal at its output 52, which signal may be regarded as "positive" or "negative," i.e. as displaced to one side or the other of a "zero" condition, these positive and negative conditions being respectively indicative of a requirement for heating or of a overheated condition requiring cooling of the oven 12. Assuming for purposes of analysis that the signal is of the "positive" polarity (indicating a heating requirement), the heater power control 54 is enabled via the control line 56, which thus actuates heater 22 to begin heating within the oven 12.

The signal from comparator 44 is also provided via line 58 to line 60, which in turn has inputs at 62 and 64 to a pair of door comparators, namely a door open comparator 66 and a door close comparator 68. These comparators are respectively associated with a door open power control 70 and a door close power control 72. Actuation of the latter instrumentalities will effect (via lines 76 or 77) operation of door motor 26 in one or the other of its directional modes.

Door comparators 66 and 68 are also provided with inputs from reference level signal sources 69 and 71, respectively. These references levels establish precisely when a signal proceding from comparator 44 is deemed of sufficient magnitude to either close or open the door 16 in the mentioned incremental amount. The use of such threshholds avoids the possibility of the system responding to noise or to such low level changes as could induce system instabilities.

The door comparators 66 and 68 are linked with their respective door power controls 70 and 72 through time delays 74 and 76, respectively. These time delays are essentially in the nature of timers, either electronic or mechanical. Their function is to delay enablement of the associated power controls for a prescribed period, in order to prevent the door power controls 70 and 72 from reacting to short responses that could be caused by the heater turning on or by a previous door opening. Only after the mentioned time delay has occurred and the polarity of the signal from comparator 44 has remained at its previous polarity (and above the reference threshhold levels) will the time delay signals cease to inhibit the power controls 70 and 72 so that enabling signals can be provided via the lines 77 and 79 to the respective power controls 70 and 72. The door open and door close power controls 70 and 72 are further provided with inputs 78 and 80 which proceed via line 82 from door position sensors 34. These are further enabling inputs for the power controls, in that the incremental opening or closing of door 16 will be effected only if the door condition (as indicated by the sensors) is not such as to already be in a fully opened or closed condition — i.e., at either end of the range 32. If enabling signals are provided from both a time delay 74 or 76 and door position sensors 34, the appropriate power control 70 or 72 is actuated for a prescribed period, which will effect an incremental actuation of the motor 26, and thus an incremental displacement of the door 16 within its operating range 32. The prescribed actuation period is determined by appropriate timer 84 or 86, which terminates operation of the associated power control 70 or 72 after the period preset in the timer. As has already been mentioned, the periods of timers 84 and 86 are chosen such that the door 16 will always seek a stable, non-oscillating position. Thus, because the times are different, the door 16 can seek an infinite number of positions based on the set point and the ambient temperature.

With the aid of the aforegoing, the operation of the present system in a typical situation may be set forth. In particular, it may be assumed that the system operator sets a temperature on control 36 of the order of a few degrees above ambient. If the sensor 20 indicates that the oven temperature is beneath the set point, heater power control 54 is actuated, which in turn enables the heater 22.

The same signal that actuates the heater control 54 appears as well in line 58, and thus is presented to the door comparators 66 and 68. As mentioned, each of these comparators is provided with its own reference level to determine when a signal is of sufficient magnitude to warrant either opening or closing of the door 16 in incremental amounts. Assuming this threshold has been exceeded so that heating of the oven 12 is indicated, an enabling signal is provided to the associated time delay 76. Thus, in this instance, if heating is still called for after the delay period, a signal will be provided to close door power control 72; and (if the door position is not already fully closed — as determined by the signal in line 82) a signal proceeds through line 76 and actuates door motor 26 for a period determined by the timer 86. This actuation of the motor 26 in turn effects an incremental rotation of shaft 27 to close the door by a stepped amount.

The fixed delays provided by the time delays 74 and 76 prevent the door controls 70 and 72 from reacting to short responses that could in the present instance be caused by the heater turning on, or by a previous door movement. If in the present instance heat were no longer needed before the end of the time delay, the door close power control 72 would simply not be enabled.

If the heat condition, i.e., the enablement of heat power control 54, were to persist after the allowed stabilization, the timer 86 would enable another incremental closing of the door 16. Further closing of the door 16 would continue in incremental steps until either the door position sensors 34 recognize a fully closed door, or until the heat request is removed — indicating a stable oven temperature.

In the inverse situation to that just illustrated, i.e., where the oven is overheated, the reverse "polarity" (or signal level) would be detected at door open comparator 66; and by a sequence of events as just described, the door 16 would be incremented open for the duration established by the timer 84. It is significant to again point out that timers 84 and 86 are intentionally provided with different timing values, the purpose of which is to assure that the door 16 will always seek a stable non-oscillating position.

Although the bi-directional door motor and actuator means 25 has been thus far described simply as incorporating a crank mechanism 28 connected to the shaft 27 of a bi-directional motor 26, in a preferable embodiment of the present invention a technique is utilized which improves the control technique heretofore discussed. The significance of this further development may be better appreciated by pointing out that although the total control range for the door 16 may include the displacement distance 32, the most effective and, so to speak, "fine control" portion of this range resides close to the position at which the oven door 16 makes contact with the enclosure 14, or with the sealing gaskets at such enclosure. This close-in range may be regarded as encompassed within the schematically indicated angle 33. In practice, it is desirable to increment the opening and closing of the door 16 by comparatively small steps within this close-in range 33, although within the more distant part of the operating range, i.e., within the range 35, a sequence of relatively "large" steps is perfectly suitable.

Figure 2:
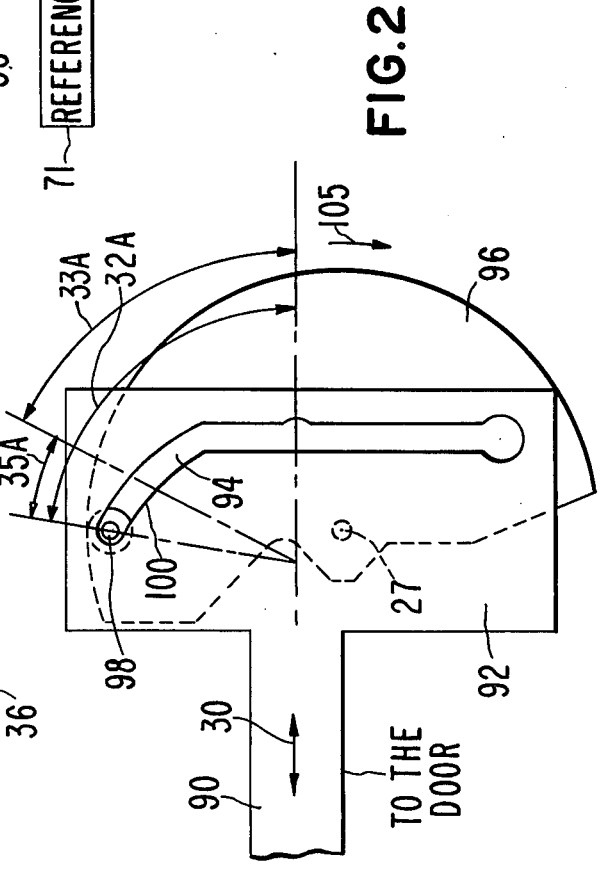
FIG. 2 is a plan view of a portion of the actuating mechanism interlinking the bi-directional door motor with the door proper, and illustrates the manner in which a desired modification of the door increments is achieved.

In accordance with this further aspect of the invention, a mechanical linkage arrangement as illustrated in the plan view of FIG. 2 may be utilized to achieve the desired result. In this arrangement, the linkage 24 which effects direct movement of the door 16 may be regarded as embodied within a link 90, i.e., the door 16 moves in one or other of the directions 30 in accordance with the movement of the link 90. Link 90, in turn, is secured to a yoke plate 92. The latter is provided with a pin receiving slot 94, so that the plate 92 essentially serves as a cam follower. A pin-carrying disc 96 underlies the plate 92, and is driven about the axis of the shaft 27 by the bi-directional door motor 26. The disc 96 carries a cam pin 98 near its periphery. This pin 98 passes through the slot 94; and during rotation of the disc 96, the yoke plate 92 moves in one or other of the direction of arrow 30 in accordance with the pin position. The slot 94 carries an appropriate curvature toward its upper end 100 so as to assure (in conjunction with the rotation of disc 96) that the desired movement characteristics for opening and closing of the door 16 are enabled. The positions, shown in FIG. 2 for the yoke plate 92 and the disc 96 respectively correspond to a relatively "fully" open door, i.e., a door which is at approximately the line 104 as shown in FIG. 1, defining the most open portion of range 32. It will be evident from consideration of the interaction between the pin 98 and the slot 94, that, as the disc 96 rotates in direction 105, relatively large incremental movements of the door 16 will initially occur, i.e., a large incremental movement for each successive equal angular displacement of the disc 96 about the axis of the shaft 27. But, it will similarly be clear that as the progressive rotation of the disc 96 in direction 105 continues, the door increments corresponding to successive angular increments i.e., decrease to smaller steps, i.e., such smaller steps occuring within the range 33 of the overall operating range 32.

It should be noted that FIG. 2 is marked with rotational displacement angles 32A, 33A, and 35A, which correspond respectively to the ranges 32, 33 and 35 in FIG. 1. Particularly to be noted is the very large rotational displacement angle 33 A, which corresponds to the relatively small close-in range 33 in FIG. 1. From this comparison it will be evident how the present arrangement serves to define sub-ranges 35 and 33 within the overall operating range 32, wherein the effects on the door opening produced by a given angular rotation of the disc 96 are relatively amplified or reduced.

While the present invention has been particularly set forth in terms of specific embodiments thereof it will be understood in view of the instant disclosure, that numerous variations upon the invention are now enabled to those skilled in the art, which variations yet reside within the scope of the present teaching. Accordingly, the invention is to be broadly construed and limited only by the scope and spirit of the claims now appended hereto.

We claim:

1. In a chromatography apparatus of the type including an oven for a chromatography column and electric heater means for controllably heating said oven, an improved system for controllably opening and closing the door of said oven to enable stabilization of the temperature in said oven at a desired set point, said system comprising:

means for generating an electrical signal that indicates by first or second conditions, respectively, whether the oven temperature is above or below said set point;

heater power control means for receiving said oven temperature indicative signal, said heater power control means being enabled by said first temperature indicative signal condition to effect heating of said oven and being inactive in response to said second temperature indicative signal condition;

bi-directional motor and actuator means for opening and closing said oven door over a prescribed operating range; and means for enabling said motor and actuator means to operate for a predetermined actuation period when said temperature indicative signal in either said first or second condition departs from a preset threshold value for each condition for a predetermined time interval, whereby to effect opening or closing of said door in incremental steps.

2. The apparatus of claim 1 wherein said means for enabling said motor and actuator means includes:

comparator means for comparing said oven temperature indicative signal with reference levels and for providing comparator output signals when said oven temperature indicative signal is above or below thresholds determined by said reference levels;

power control means for actuating said bi-directional motor and actuator means, said power control means being at least in part enabled by said comparator output signals to actuate said bi-directional motor and actuator means; and time delay means coupled between said comparator means and said power control means to prevent application of said comparator output signals to said power control means prior to the expiration of a prescribed time delay interval.

3. The apparatus of claim 2 wherein said predetermined time interval is established by timer means associated with said comparator means for providing control signals to said power control means to limit the period of operation of said power control means and thereby to limit the incremental stepwise movement of said door.

4. The apparatus of claim 3 wherein said comparator means comprises a first comparator for providing a comparator output signal when said oven temperature indicative signal indicates an oven temperature above said set point and a second comparator for providing a comparator output signal when said oven temperature indicative signal indicates an oven temperature below said set point, and wherein said timer means comprises first and second timers associated, respectively, with said first and second comparators, said timers having different durational intervals to thereby inhibit generation of oscillatory modes in the opening and closing of said door.

5. The apparatus of claim 4 further including door position sensor means for determining whether said door is within the limits of said prescribed operating range, said door position sensor means being coupled to said heater power control means to enable operation of said heater power control means when said door is within said prescribed operating range.

6. In a chromatography apparatus of the type including an oven for a chromatography column of said apparatus, and electric heater means for controllably heating said oven, an improved system for controllably opening and closing the door of said oven to enable a controlled heat flow to thereby stabilize the temperature of said oven at a desired set point, said system comprising:

heat sensor means at said oven for generating a signal indicative of the temperature in said oven;

first comparator means for comparing said oven temperature indicative signal with said set point temperature and generating an output signal at first or second relative polarities indicative, respectively, of departure of the temperature of said oven in a positive or negative direction from said set point;

heater power control means for receiving the output signal from said first comparator means, said heater power control means being enabled when said first comparator means output signal is at said first relative polarity to effect heating of said oven and being inactive when said first comparator means output signal is at said second relative polarity;

bi-directional motor means for opening and closing said oven door over a prescribed operating range;

first and second reference level signal generators for providing first and second threshold signals, respectively;

door open comparator means and door close comparator means for receiving the threshold signals from said first and second reference level generators and for receiving the output signal from said first comparator means, said door open comparator means providing an output signal when said first comparator means output signal is above said first threshold signal, and said door close comparator means providing an output signal when said first comparator means output signal is below said second threshold signal;

door open power control means and door close power control means connected to actuate said bi-directional motor means in the directions effective to open and close said oven door;

the output signals from said door open and said door close comparator means serving to enable said door open and said door close power control means, respectively, through time delay means, whereby an enabling output signal from said door open comparator means or from said door close comparator means is provided to said door open power control means or to said door close power control means only when said enabling signal extends for the duration of the delay provided by said time delay means; and timer means associated with said door open and said door close power control means for limiting the period of operation of said door open and said door close power control means to thereby enable incremental stepwise movement of said oven door.

7. The apparatus of claim 6 wherein said timer means comprises a separate timer associated with each of said door open and close power control means, said timers having different durational intervals to thereby inhibit the generation of oscillatory modes in the movement of said oven door during said stepwise movement.

* * * * *